United States Patent [19]

Van Der Heijden et al.

[11] Patent Number: 5,952,430
[45] Date of Patent: *Sep. 14, 1999

[54] PROCESS FOR SELECTIVE HYDROGENATION OF POLY(MONOVINYL AROMATIC)-POLY(CONJUGATED DIENE) BLOCK COPOLYMERS

[75] Inventors: Harry Van Der Heijden; Bart Hessen, both of Amsterdam, Netherlands

[73] Assignee: Shell Oil Company, Houston, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/935,507

[22] Filed: Sep. 23, 1997

[30] Foreign Application Priority Data

Sep. 24, 1996 [EP] European Pat. Off. .............. 96306949

[51] Int. Cl.⁶ .............. C08C 19/02; C08F 8/02; C08F 8/42; C08F 8/04
[52] U.S. Cl. .............. 525/338; 525/339; 526/943
[58] Field of Search .............. 502/103, 117, 502/152, 155, 158; 525/338, 339

[56] References Cited

U.S. PATENT DOCUMENTS

| | | | |
|---|---|---|---|
| 3,036,048 | 5/1962 | Von Falkai et al. .............. | 260/78.4 |
| 4,501,857 | 2/1985 | Kishimoto et al. .............. | 525/338 |
| 4,673,714 | 6/1987 | Kishimoto et al. .............. | 525/338 |
| 4,980,421 | 12/1990 | Teramoto et al. .............. | 525/338 |
| 5,036,034 | 7/1991 | Ewen .............. | 502/117 |
| 5,039,755 | 8/1991 | Chamberlain et al. .............. | 525/338 |
| 5,132,372 | 7/1992 | Chamberlain et al. .............. | 525/338 |
| 5,141,997 | 8/1992 | Chamberlain et al. .............. | 525/338 |
| 5,153,157 | 10/1992 | Hlatky et al. .............. | 502/117 |
| 5,162,446 | 11/1992 | Gibler et al. .............. | 525/338 |
| 5,169,905 | 12/1992 | Hashiguchi et al. .............. | 525/339 |
| 5,173,537 | 12/1992 | Chamberlain et al. .............. | 525/338 |
| 5,206,307 | 4/1993 | Chamberlain et al. .............. | 525/339 |
| 5,387,568 | 2/1995 | Ewen et al. .............. | 502/104 |
| 5,496,960 | 3/1996 | Piers et al. .............. | 556/8 |
| 5,753,778 | 5/1998 | Ko et al. .............. | 525/338 |
| 5,886,107 | 3/1999 | De Boer et al. .............. | 525/339 |
| 5,886,108 | 3/1999 | Miyamoto et al. .............. | 525/339 |

FOREIGN PATENT DOCUMENTS

| | | | |
|---|---|---|---|
| 0 426 637 | 5/1991 | European Pat. Off. . | |
| 0 427 697 | 5/1991 | European Pat. Off. . | |
| 434469 | 6/1991 | European Pat. Off. . | |
| 0 544 304 | 6/1993 | European Pat. Off. .............. | 525/339 |
| 545844 | 6/1993 | European Pat. Off. . | |
| 554574 | 8/1993 | European Pat. Off. . | |
| 61-28507 | 2/1986 | Japan .............. | 525/339 |
| 62-207303 | 9/1987 | Japan .............. | 525/339 |
| 62-209102 | 9/1987 | Japan .............. | 525/339 |
| 62-209103 | 9/1987 | Japan .............. | 525/339 |
| 3-33107 | 2/1991 | Japan .............. | 525/339 |
| 4-96904 | 3/1992 | Japan .............. | 525/339 |
| 4-96905 | 3/1992 | Japan .............. | 525/339 |
| 94/25416 | 11/1994 | WIPO . | |
| WO 95/12622 | 5/1995 | WIPO . | |
| 95/25130 | 9/1995 | WIPO . | |

OTHER PUBLICATIONS

X. Yang et al., Angew. Chem. Int. Ed. Engl. 1992, vol. 31, No. 10, pp. 1375–1377.
H. Brintzinger et al., Angew. Chem. Int. Ed. Engl. 1995, vol. 34, pp. 1143–1170.
X. Yang et al., J. Am. Chem. Soc., vol. 113, No. 9, pp. 3623–3625, 1991.
X. Yang et al., J. Am. Chem. Soc., vol. 116, No. 22, pp. 10015–10031, 1994.
Y.–X. Chen et al., J. Am. Chem. Soc., vol. 119, No. 10, pp. 2582–2583, 1997.

Primary Examiner—Mark L. Bell
Assistant Examiner—J. Pasterczyk
Attorney, Agent, or Firm—Donald F. Haas

[57] ABSTRACT

This invention is a process for the selective hydrogenation of block copolymers having at least one poly(vinyl aromatic) block and at least one poly(conjugated diene) block which comprises contacting the block copolymers with hydrogen in the presence of a hydrogenation catalyst composition which comprises:

a) a metal compound cation of the formula $[(A)(E)M(R_4)]^+$ wherein M represents titanium, zirconium, or hafnium, A and E each represent ligands with structure I or II

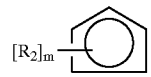 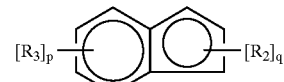

Structure I          Structure II in which $R_1$ independently represents the same or different hydrocarbyl groups optionally containing heteroatoms, and $R_3$ independently represents the same or different hydrocarbonyl groups optionally containing heteroatoms, or a halide, and in which $R_1$ and $R_3$ may be shared between A and E to provide a bridge, wherein m is an integer from 0–5, p is an integer from 0–4, and q is an integer from 0–3, wherein $R_4$ represents hydrogen or hydrocarbyl group optionally containing heteroatoms, with the proviso that if A and E are both ligands with the same structure, at least one of m, p or q is at least 1, and b) a non-coordinating stable anion.

9 Claims, No Drawings

PROCESS FOR SELECTIVE HYDROGENATION OF POLY(MONOVINYL AROMATIC)-POLY(CONJUGATED DIENE) BLOCK COPOLYMERS

FIELD OF THE INVENTION

The present invention relates to a process for the hydrogenation of olefins in general and in particular to polymers or oligomers of conjugated diene, and to catalysts usable therefor, as well as to a process for the preparation of catalysts. More in particular the invention relates to a process for the hydrogenation of olefins or oligomers, polymers or copolymers of conjugated diene polymers, having one or more substituents attached to one of the double bond carbon atoms, using a hydrogenation catalyst comprising at least a group 4 transition metal complex.

BACKGROUND OF THE INVENTION

Numerous catalyst are known for the hydrogenation of compounds containing unsaturated double bonds, catalysts which may be classified into two groups:
(1) Heterogeneous catalysts, generally consisting of a metal such as Ni, Pd, Pt, Ru, etc. optionally deposited on a support such as carbon, silica, alumina, calcium carbonate, etc.; and
(2) homogeneous catalysts such as (a) Ziegler catalysts consisting of a combination of an organic salt of Ni, Co, Fe, Cr, etc. and a reducing agent such as the organoaluminium compounds and the like, and (b) single component organometallic compounds of Ru, Rh, Ti, La, etc.

U.S. Pat. No. 4,501,857 describes a hydrogenation catalyst in which one of the components is a derivative of cyclopentadienyltitanium—necessarily in the presence of organolithium compounds—for the hydrogenation of the olefinic double bonds of the polymers of conjugated dienes.

European Patent application publication Nos. 0460725, 0549063, 0434469, 0544304, 0545844 and 0601953, International application Nos. WO 96/18660 and WO 96/18655, and British patent application No. 2159819 also describe homogeneous titanium-containing hydrogenation catalyst compositions.

International application No. WO 95/25130 discloses a process for selective hydrogenation of unsaturated polymers containing aromatic and olefinic carbon—carbon double bonds, using as catalyst complex of a metallocene compound, comprising zirconium connected to two substituted or unsubstituted cyclopentadienyl or indenyl groups and to two other ligands selected from halogen, lower alkyl or benzyl, and an alumoxane and preferably methylalumoxane, in a molar ratio of zirconium metal to aluminium metal in the catalyst complex of from 50–500.

However, as known from e.g. European patent application publication No. 0584860, known hydrogenation processes still have as a general shortcoming that in block copolymers, comprising at least blocks formed by poly(conjugated diene) in which the constituting monomer was a branched alkadiene of from 5 to 10 carbon atoms and bearing at least one alkyl substituent to one of carbon atoms of the remaining double bonds, could not be completely or substantially hydrogenated under the usual hydrogenation conditions.

More particularly, said shortcoming is the reason why the known catalysts were satisfactory for the selective hydrogenation of poly(styrene)-poly(butadiene) block copolymers, but not for block copolymers comprising poly(isoprene) blocks or blocks wherein isoprene is a comonomer.

It will be appreciated that the same can be stated for other substituted poly(alkadienes) as well as tri- or tetra-substituted olefins.

The shortcomings of these catalysts are not limited to the hydrogenation of polymeric substrates as described above. The shortcomings extend to low-molecular weight substrates containing similarly substituted double bonds as well, as is exemplified by the work of Broene and Buchwald (J.Am. Chem. Soc. 1993, 115, 12569). Furthermore, the work by Marks et al, as disclosed in U.S. Pat. No. 4,668,773 shows that hydrogenation of olefinic bonds with more than two substituents is indeed a very difficult reaction for which no efficient homogeneous catalysts are known.

It will be appreciated that there is a need for homogeneous "all purpose" catalysts which may hydrogenate all types of olefinic substrates, including the poly(conjugated diene) blocks in block copolymers, in an economical way with respect to catalyst costs (by use of low concentrations) and process time (preferably less than one hour for hydrogenation of more than 80% of the original double bonds and preferably more than 95% and more preferably more than 98%).

SUMMARY OF THE INVENTION

One object of the present invention is formed by an improved hydrogenation process and another object is formed by a catalyst composition for use in said process. As a result of extensive research and experimentation such catalyst and process have surprisingly been found.

Accordingly, the present invention relates to a catalyst composition which comprises at least:

a) a metal compound cation of the formula:

wherein M represents titanium, zirconium, or hafnium, wherein A and E represent ligands with structure I or II

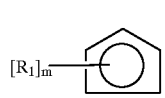
Structure I

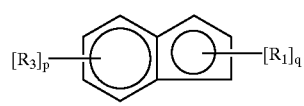
Structure II in which $R_1$ independently represents the same or different hydrocarbyl groups optionally containing heteroatoms, and $R_3$ independently represents the same or different hydrocarbyl groups optionally containing heteroatoms, or a halide, and in which R substituents may be shared between A and E to provide a bridge, wherein m is an integer from 0–5, p is an integer from 0–4, and q is an integer from 0–3, wherein $R_4$ represents hydrogen or hydrocarbyl group optionally containing heteroatoms, with the proviso that if A and E are both ligands with the same structure, at least one of m, p or q is at least 1, b) a non-coordinating stable anion.

DETAILED DESCRIPTION OF THE INVENTION

Preferably the metal compound cation has structure III

Structure I wherein M=titanium or zirconium, wherein A=a ligand with the same structure in which $R_1$ and $R_2$ are independently the same or different hydrocarbyl optionally containing a heteroatom and $R_3$ is hydrocarbyl, optionally containing a heteroatom, or a halide; $R_2$ may combine with $R_1$ or $R_3$ to form a bridge;
wherein m is an integer from 0–5, p is an integer from 0–4, and q is an integer from 0–3, and n is an integer from 1–5; wherein $R_4$ represents hydrogen or hydrocarbyl group optionally containing heteroatoms.

More preferably, $R_2$ is a branched hydrocarbyl of from 3 to 15 carbon atoms and optionally containing heteroatoms.

According to a further preferred embodiment the present invention relates to a catalyst composition which comprises at least:
(a) a metal compound cation of the formula:

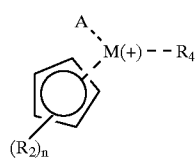

wherein M represents zirconium, titanium or hafnium, wherein A represent a cyclopentadienyl group of the formula

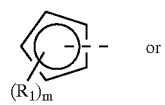 or an indenyl group of the formula

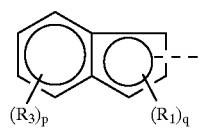

wherein each $R_1$ independently represents the same or different alkyl groups having from 1 to 4 carbon atoms, wherein each $R_2$ independently represents the same or different bulky molecular structure formed by an alkyl group, having from 3 to 10 carbon atoms, an aryl group having from 6 to 20 carbon atoms, which itself may optionally be substituted by lower alkyl group(s) having from 1 to 3 carbon atoms or halogen, cycloalkyl groups having from 5 to 8 carbon atoms and which optionally may be substituted by lower alkyl group(s) having from 1 to 3 carbon atoms or halogen, aralkyl groups having from 7 to 14 carbon atoms which may optionally be substituted by lower alkyl group(s) having from 1 to 3 carbon atoms or halogen, or by optionally substituted alkyl groups or heteroatoms containing groups, such as —Si($C_1$–$C_3$ alkyl)$_3$, ~Si(phenyl)$_3$, ~N(phenyl)$_2$, ~NH(phenyl), ~B(phenyl)$_2$ and ~B(phenoxy)$_2$, wherein each of $R_3$ independently may be selected from halogen, phenyl which optionally may be substituted, lower alkyl (1–3 carbon atoms), lower alkoxy (1–3 carbon atoms), phenoxy, phenylalkoxy or benzyl, wherein p may be an integer from 0 to 4, wherein m represents an integer in the range of from 1 to 5 and preferably from 3 to 5, wherein q represents an integer in the range of from 1 to 3 and n represents an integer from 1 to 5, and preferably 1, wherein $R_4$ represents hydrogen, an alkyl group of from 1 to 10 carbon atoms, an aryl group of from 6 to 18 carbon atoms, arylalkyl of from 7 to 24 carbon atoms or an optionally substituted allyl group, and
(b) a non-coordinating stable anion.

Moreover the present invention relates to a process for the hydrogenation of polymers containing ethylenic unsaturation, preferably at least one of the monomers constituting the polymer comprises at least one carbon atom which has been substituted, which process uses the hereinbefore specified catalysts.

According to a further preferred embodiment of the catalyst, M represents zirconium or titanium, $R_1$ represents a lower alkyl of from 1 to 3 carbon atoms and most preferably methyl, m has a value of 5, and q has a value of 3, $R_2$ represents a hydrogen or a hydrocarbyl group, n is 1, $R_3$ represents lower alkyl or lower alkoxy and p=0, 1 or 2, and preferably 0.

More preferably $R_2$ is a bulky substituent, selected from the group consisting of phenyl, o-tolyl, 2,6-xylyl, p-tert butyl phenyl, 2,6(isopropyl), m-phenyl dichlorophenyl, 3,5-di(tert butyl)-4 methoxy-phenyl, dimethylphenyl methyl, tert butyl, iso propyl, iso butyl and cyclo pentyl or cyclo hexyl, trimethylsilyl, dimethyl tert.butylsilyl, tri(phenyl) silyl, di phenyl amine, diphenyl boryl. Most preferably $R_2$ is tert butyl or trimethylsilyl and m=1.

In the most preferred embodiments of the present catalyst L represents hydrogen, methyl, ethyl, n propyl, n-butyl, neopentyl, dimethylphenylmethyl, benzyl, phenyl, allyl or substituted allyl and most preferably methyl.

The non-coordinating stable anion can be derived from a variety of borium containing compounds.

Examples of such compounds are known from literature, e.g. Marks et al, Organometallics 1995, 14, 3135.

Preferably, the non-coordinating stable anion is a carborane anion, suitably a carborane anion of the formula $[B_{11}CH_{12}^-]$. Such carboranes are known and can be prepared by methods such as that of K. Shelly et al. (J. Am. Chem. Soc. 107, 1985, 5955).

More preferably anions of formula

are used, wherein Ar represents a strongly electron withdrawing hydrocarbyl group, preferably a phenyl group substituted with strongly electron withdrawing substituents, such as halogen or alkoxy having from 1 to 3 carbon atoms or a trihalogen substituted methyl. R represents Ar or a group which is typically the same as represented by $R_4$, that is hydride or a hydrocarbyl group, optionally containing heteroatoms. Most preferably the non-coordinating stable anion has the formula $[B(Ar)_4^-]$, and Ar represents

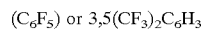

Without being bound to a definite theory it is presumed that the hereinbefore specified hydrogenation catalysts may derive their unique effectiveness from their ability to perform C—H activation. This ability allows metal alkyl species which are formed during the reaction to form alkanes and in addition may allow isomerisatin of tri- and tetra-substituted olefins to less-hindered disubstituted olefins which can be readily hydrogenated.

The catalyst composition is typically obtainable by reacting a metal compound of formula $(A)(B)MR_{42}$, wherein A,B,M and each $R_4$ independently are as defined herein (precursor component (a)), with a salt of a non-coordinating stable anion (precursor component (b)).

Preferably, the salt of the non-coordinating stable anion is $G^+[B(Ar)_4]^-$ or $B(Ar)_3$ in which Ar is as defined herein and G is a cation capable of reacting with one L of the metal compound to form a compound GL.

Preferably, the compound GL, hereinafter termed the elimination product, is not interfering with the later hydrogenation reaction or can easily be removed from the actual catalyst.

Examples of suitable cations G are $PhNMe_2H^+$ or $Ph_3C^+$. Examples of suitable elimination products are triphenyl ethane, generated by reaction of a Group 4 metallocene dimethyl compound with a tritylium salt of a non-coordinating anion, or methane, generated by reaction of a Group 4 metallocene dimethyl compound with a dimethylanilinium salt of a non-coordinating anion. The molar ratio of the precursor components (a) and (b) may typically vary in the range of from 1:5 to 5:1 and, preferably, 1:1.

Thus, according to a further aspect, the present invention relates to a process for the preparation of a catalyst composition, which comprises reacting a metal compound of the formula $(A)(E)ML_2$ as defined herein, with a salt of a non-coordinating stable anion as defined herein.

The catalyst compositions of the present invention may be prepared prior to the actual hydrogenation process, i.e. contacting with hydrogen and the polymer containing the ethylenic unsaturation, or they may be prepared in situ, i.e. in the presence of the hydrogen and the polymer cement, from which a substantial part of the previously formed (during termination) lithium compound has been removed before.

It will be appreciated that according to another more preferred embodiment, the formation of an insoluble easily separable lithium compound such as lithium chloride, will be aimed at simultaneously with and interrelated to the formation of the catalyst components (a) and (b) from suitably selected precursor compounds.

It will be appreciated that the catalyst compositions and the process for hydrogenation according to the present invention have surprisingly shown to enable the complete hydrogenation of ethylenic unsaturation.

Accordingly, an advantage of the present hydrogenation process and catalyst is that not only homopolymers or block copolymers containing polymerised linear conjugated diene can be (selectively) hydrogenated, but also homopolymers of branched conjugated diene or block copolymers having at least one poly(monovinyl-aromatic) block and at least one poly (branched conjugated diene) block, and preferably poly(isoprene) homopolymers or poly(styrene)-poly (isoprene) block copolymers, can be hydrogenated effectively with a very high selectivity towards olefinic unsaturation. Hydrogenation degrees of 95% or more of the original olefinic unsaturation may be reached with periods of less than 3 hours and preferably from 0.5 to 1 hour.

The hydrogenation process can be performed at partial hydrogen pressures in the range of from 0.1 to 100 bar and preferably from 1–35 bar.

Included in the above branched conjugated diene polymers are branched conjugated diene homopolymers and copolymers produced from branched conjugated dienes and non branched conjugated dienes or from at least one branched conjugated diene and at least one olefin copolymerisable with the branched conjugated diene.

Given as typical examples of conjugated dienes used for the production of these branched conjugated diene oligomers or polymers are conjugated dienes having 5–12 carbon atoms. Specific examples are isoprene, 2,3-dimethyl-1,3-butadiene, 2-methyl-1,3-pentadiene, 4,5-diethyl-1,3-octadiene, 3-butyl-1,3-octadiene, and chloroprene.

In particular, from the aspect of manufacturing hydrogenated elastomers with industrial advantages, homopolymers of isoprene, block copolymers comprising at least one block derived from isoprene monomer alone or optionally mixed with another suitable linear conjugated diene can be prepared in an economically attractive way. However, said block copolymers may comprise in addition blocks of other branched and/or linear conjugated dienes and/or pure monovinyl aromatic monomer blocks or tapered or random polymerised blocks of isoprene and a monovinyl aromatic monomer and preferably styrene.

Hydrocarbon solvents used in the hydrogenation reaction may be aliphatic hydrocarbons, e.g., pentane, hexane, heptane, octane, etc.; alicyclic hydrocarbons, e.g., cyclopentane, methyl cyclopentane, cyclohexane, etc. or aromatic solvent such as toluene, or, preferably, bromobenzene.

There are no restrictions as to the concentration of polymers in carrying out the hydrogenation reaction of the present invention. Usually, the polymer concentration is 1–30% by weight, and preferably 3–20% by weight. The hydrogenation reaction is effected, after the addition of the hydrogenation catalyst composition under an inert gas atmosphere, e.g., in nitrogen or argon, or under a hydrogen atmosphere, by supplying hydrogen, with or without stirring while maintaining the temperature of the polymer solution at a specified temperature.

A temperature suitable for the hydrogenation reaction is 0–150° C. A temperature lower than 0° C. is uneconomical, since at a temperature lower than 0° C. not only the catalyst activity is lowered, but also the rate of hydrogenation is retarded. If the temperature is higher than 150° C., the polymers tend to decompose or to gel. A more preferred temperature range is 10–100° C., and particularly preferred is 15–75° C.

The hydrogenation reaction usually is carried out within a time period of from 0.1 hr to 3 hrs. The larger the amount of the catalyst composition used and the higher the hydrogen pressure, the shorter the reaction time may be.

Usually applied catalyst concentrations per 100 g of polymer to be hydrogenated will be in the range of from 0.01 g to 1 g Zr, Hf or Ti metal, and preferably from 0.19–0.75 g Zr, Hf or Ti metal per 100 g polymer.

The invention can be illustrated by the following examples without however restricting the scope of the invention to these specific embodiments.

EXAMPLES

The following catalyst precursors were prepared.
(A) Preparation of $Cp^*Cp^tBuZr(Me)_2$ wherein $Cp^*= \eta5:C_5Me_5$, Me=methyl and $^tBu$=tert-butyl, Cp=cyclopentadienyl or substituted cyclopentadienyl $[Cp(Me)_5]ZrCl_3$ (1.763 g, 5.30 mmol) and $(Cp^tBu)Li$ (691 mg, 5.38 mmol) were weighed into a Schlenk-vessel. The flask was cooled to 196° C. and mesitylene (50 mL) was added. The suspension was slowly allowed to warm to room temperature and subsequently heated to 120° C. After being stirred for 22 h at 120° C., the mesitylene was removed in vacuo. The yellow residue was suspended in diethylether (40 mL). MeLi (6.95 mL, 11.1 mmol) was dropwise added at room temperature. The suspension was stirred for another 18 h at room temperature. The diethylether was removed in vacuo and the residue was extracted with pentane (40 mL). Filtration, concentration and crystallisation at −30° C. gave [Cp(Me)$_5$](Cp$^t$Bu)ZrMe$_2$ (688 mg, 1.81 mmol) as white needles. A second crystallisation gave another portion, which, however, was contaminated with a yellow oil. The oil was partly removed by washing the crystals with two small portions of cold pentane. Total yield: 971 mg (2.57 mmol, 52%).

(B) Preparation of Cp* Cp[(Me)$_3$ Si]$_2$ ZrMe$_2$.

This compound was prepared in the same way as described under (A) starting from [Cp(Me)$_5$]ZrCl$_3$ and Cp[(Me)$_3$Si]$_2$, to which subsequently MeLi was added.

(C) Preparation of Cp*Cp($^t$Bu)TiCl$_2$ 1.09 gram of Cp*TiCl$_3$ (3.77 mmol) was dissolved in 25 mL of CH$_2$Cl$_2$ and cooled to −40° C. 0.53 gram of ($^t$Bu)Cp lithium (3.77 mmol) was added and the reaction mixture was slowly brought to room temperature. After stirring for 16 h, the reaction mixture was centrifugated and the CH$_2$Cl$_2$ was removed in vacuo. 1.39 gram of Cp*Cp($^t$Bu)TiCl$_2$ (98%) was obtained as a purple crystalline compound.

$^1$H-NMR (CD$_2$Cl$_2$): δ6.16 (t, $^3J_{HH}$=2.7 Hz, 2, CpH), 5.89 t, $^3J_{HH}$=2.7 hZ, 2cPh); 1.9 (S, 15, C$_5$Me$_5$); 1.28 (S, 9, C(CH$_3$)$_3$)$_3$ $^{13}$C-NMR(CD$_2$Cl$_2$): δ149.8 (Cp$^t$BU$_{IPSO}$); 129.5 (C$_5$Me$_5$); 120.9 (Cp$^{tBU}$); 114.2 (Cp$^t$BU); 34.2 (C(CH$_3$)$_3$); 30.5 (C(CH$_3$)$_3$); 13.1 (C$_5$(Me)$_5$)

(D) Preparation of Cp*.Cp (tBu)Ti Me$_2$ 846 mg of Cp*Cp($^{tBu}$)TiCl$_2$ (2.28 mmol) in 20 mL of diethylether was cooled to −78° C. 2.85 mL of a 1.6 M solution of MeLi in ether (4.55 mmol) was added. The reaction mixture was allowed to warm slowly to room temperature. The yellow coloured reaction mixture was evaporated to dryness and extracted with pentane. Removal of the pentane gave 0.51 gram (67%) of Cp*Cp($^{tBu}$)TiMe$_2$ as yellow coloured crystals.

$^1$H-NMR (C$_5$D$_6$); δ5.90 (t, $^3J_{HH}$=2.6 Hz, 2, CpH), 5.36 (t, $^3J_{HH}$=2.6 Hz,2,CpH); 1.68(s,15, C$_5$Me$_5$); 1.28 (s,9,C(CH$_3$)$_3$); −0.15 (s,6,Ti(CH$_3$)$_2$)

$^{13}$C-NMR (C$_6$D$_6$) δ142.2 (Cp$^{tBu}$$_{ipso}$); 119.5 (Cp$^{tBu}$); 112.7 (C$_5$Me$_5$); 110.0 (Cp$^{tBu}$); 45.6 (TiCH$_3$); 33.6 C(CH$_3$)$_3$); 31.2 (C(CH$_3$)$_3$); 11.9 (C$_5$Me$_5$)

(E) Preparation of Cp Ind Ti(benzyl)$_2$

To a suspension of 981.6 mg of CpIndTiCl$_2$ (3.28 mmol) in 50 mL of ether was added 849 mg of Mg(CH$_2$Ph)$_2$ 0.5 dioxane (3.28 mmol). The reaction was stirred overnight, filtered and evaporated to dryness.

$^1$H-NMR(C$_6$D$_6$) δ7.23 (d,$^3J_{HH}$=8 Hz, 2, benzyl-H$_m$), 7.15 (m, H(ind), 2); 6.9 (m, H(ind) +benzyl-Hp,6); 6.8 (d,$^3J_{HH}$=8 Hz, 2); 6.07 (d, $^3H_{HH}$=3.5 Hz, 2, CpH); 5.88 (t, $^3J_{HH}$=3.5 Hz, 1, CpH); 5.38 (s, 5, CpH); 1.5 (AB-pattern, $^2J_{HH}$=8.9 Hz, TiCH$_2$)

$^{13}$C-HMR (C$_6$D$_6$) 6 153.6 (benzyl$_{ipso}$); 126.2; 126.1 (benzyl$_{ortho}$); 125.7 (benzyl$_{meta}$); 125.1; 121.8; 119.0 (benzyl$_{para}$); 116.5; 115.0 ((C$_5$H$_5$)$_2$TiBz$_2$); 106.0; 76.9 (TiCH$_2$)

The following hydrogenation experiments were carried out:

Example 1

A pressure bottle was charged with 9.1 mg of Cp*Cp($^t$Bu) ZrMe$_2$ (24 μmol), 20.5 mg of [Ph$_3$C][B(C$_6$F$_5$)$_4$] (22 μmol) in 1 mL of bromobenzene, followed by 0.84 mL of 2,4,4-trimethyl-2-pentene (5.39 mmol) and 3 mL of bromobenzene. The hydrogenation was conducted for 10 min. under 1 bar of hydrogen at room temperature.

GC-analysis:99.9% of olefin hydrogenated

Example 2

To a pressure bottle charged with 402 mg of poly-isoprene in 2 mL of bromobenzene was added a mixture of 9.2 mg of Cp*Cp(tBu)ZrMe$_2$ (24 μmol) and 20.6 mg of [Ph$_3$C][B(C$_6$F$_5$)$_4$](22 μmol) in 1 mL of bromobenzene. The bottle was placed under 1 bar of H$_2$ and stirred for 45 mn. $^1$H-NMR showed full conversion.

Example 3

To a pressure bottle charged with 316 mg of poly-isoprene in 2 mL of bromobenzene was added a mixture of 7.0 mg of Cp*Cp($^{tBu}$)ZrMe$_2$ (18.5 μmol) and 14.9 mg of [PhNMe2H][B(C$_6$F$_5$)$_4$] (18.6 μmol) in 1 mL of bromobenzene. The bottle was placed under 1 bar of H$_2$ and stirred for 45 min. $^1$H-NMR showed full conversion.

Example 4

To a pressure bottle charged with 303 mg of poly-isoprene in 2 mL of bromobenzene was added a mixture of 10.3 mg of Cp*Cp [(Me)$_3$Si)$_2$ZrMe$_2$ (22 μmol) and 18.5 mg of [Ph$_3$C][B(C$_6$F$_5$)$_4$] (20 μmol) in 1 mL of bromobenzene. The bottle was placed under 1 bar of H$_2$ and stirred for 16 hours. $^1$H-NMR showed >98% conversion.

Example 5

A pressure bottle was charged with 8.5 mg of Cp*Cp($^t$Bu) TiMe$_2$ (25.4 μmol), 21.6 mg of [Ph$_3$C][B(C$_6$F$_5$)$_4$] (23.4 μmol) in 1.0 mL of bromobenzene, followed by 0.78 mL of 2,4,4-trimethyl-2-pentene (5.1 mmol, 200 equivalents) and 3 mL of bromobenzene. The hydrogenation was conducted for 0.5 hour under 1 bar of hydrogen.

GC-analysis: 80.5% of olefine hydrogenated.

Example 6

To a pressure bottle charged with 273 mg of poly-isoprene in 2 mL of bromobenzene was added 8.6 mg of Cp*Cp($^t$Bu) TiMe$_2$ (25.7 μmol) and 21.8 mg of [Ph$_3$C][B(C$_6$F$_5$)$_4$] (23.7 μmol) in 1 mL of bromobenzene. The bottle was immediately placed under 1 bar of H$_2$ and stirred for 0.5 hour. $^1$H-NMR showed about 50% conversion.

Example 7

A pressure bottle was charged with 9.5 mg of Cp*Cp($^t$Bu) TiMe$_2$ (28.4 μmol), 22.8 mg of [PhNMe$_2$H][B(C$_6$F$_5$)$_4$] (28.4 μmol) in 1.0 mL of bromobenzene, followed by 0.90 mL of 2,4,4-trimethyl-2-pentene (5.8 mmol, 206 equivalents) and 3 mL of bromobenzene. The hydrogenation was conducted for 0.5 hour under 1 bar of hydrogen.

GC-analysis: 28% of olefine hydrogenated.

Example 8

To a pressure bottle charged with 11.3 mg of indenyl cyclopentadienyl titanium dibenzyl (22.2 μmol) and 18.9 mg of [Ph$_3$C][B(C$_6$F$_5$)$_4$] (20.5 μmol) in 1 mL of bromobenzene, was added 0.86 mL of 2,4,4-trimethyl-2-pentene (5.5 mmol, 200 equivalents) and 2 mL of bromobenzene. The reaction was conducted for 0.5 hour under 1 bar of hydrogen.

GC-analyses showed 99% of the olefin hydrogenated.

Example 9

To a pressure bottle charged with 287 mg of poly-isoprene (4.2 mmol, 187 equivalents) in 2 mL of bromobenzene was added 9.6 mg of indenyl cyclopentadienenyl titanium dibenzyl (23.4 μmol) and 19.9 mg of [Ph$_3$C][B(C$_6$F$_5$)$_4$] (21.5 μmol) in 1 mL of bromobenzene. The bottle was immediately placed under 1 bar of H$_2$ and stirred for 0.5 hour. $^1$H-NMR showed about 20% conversion.

Example 10

A NMR tube was charged with 5.5 mg of Cp*Cp$^t$BuZrMe$_2$ (14.5 μmol), 12.6 mg of [Ph$_3$C][B(C$_6$F$_5$)$_4$] (13.6 μmol), 36 mg of 2,3-dimethyl-2-butene (0.42 mmol, 30 equivalents) in 0.5 mL of bromobenzene-d$_5$. After 1 hour, ≈15% of 2,3-dimethyl-2-butene was hydrogenated to 2,3-dimethylbutane (about 15 mL of H$_2$ was added by syringe).

Example 11

A NMR tube was charged with 7.3 mg of indenyl cyclopentadienyl titanium dibenzyl (17.8 μmol), 16.4 mg of [Ph$_3$C][B(C$_6$F$_5$)$_4$] (17.8 μmol), 83.9 mg of polyisoprene (1.22 mmol, 69 equivalents) in 0.5 mL of bromobenzene-d$_5$. After 1 hour, >90% of the double bonds were hydrogenated (about 30 mL of H$_2$ was added by syringe).

Comp. Example (a)

A similar experiment as in Example 11 was conducted with bis-cyclopentadienyl titanium dibenzyl, but no conversion of polyisoprene was observed.

Comp. Example (b)

A NMR tube was charged with 8.5 mg of indenyl cyclopentadienyl titanium dibenzyl (10.7 μmol), 5 mL of H$_2$ and 0.5 mL of C$_6$D$_6$. After 1 hour, 50 mg of polyisoprene (0.73 mmol, 35 equivalents) was added to the reaction mixture together with 8 mL of H$_2$. $^1$H-NMR showed only hydrogenation of the 1,2-double bonds.

Example 12

To a pressure bottle charged with 0.86 ml of 2,4,4-trimethyl-2-pentene-2(5.5 μmMol) and 3 ml of bromobenzene were added 6.2 mg of Cp$^{tBU}$(1,3-Ph$_2$-Me-indenyl)TiMe$_2$ and 11.2 mg of [Ph$_3$C$^+$][B(C$_6$F$_5$)$^-_4$]. The bottle was immediately placed under 1 bar of H$_2$ and stirred for one hour. Analyzes showed 100% conversion of olefin to 2,4,4-trimethylpentane.

Example 13

To a pressure bottle charged with 8.0 mg of Cp$^{tBU}$Cp*ZrMe$_2$ and 20.0 mg of [PhNMe$_2$H$^+$][B(C$_6$F$_5$)$^-_4$] was added 0.45 g of 1-CD$_3$C$_6$H$_9$ (trideuteromethylcyclohexene) at room temperature. The bottle was immediately pressurised with 5 bar of H$_2$. After 45 minutes continuously stirring, the reaction was stopped and the products analysed. Olefin was converted for more than 98% to afford trideuteromethylcyclohexane.

Example 14

To a 10.7 mg of 1,1'-ethylenebisindenyl zirconium dimethyl (EtInd$_2$ZrMe$_2$), (25.8 μmol) (containing approx. 0.5 equivalent of diethylether) in an NMR tube was added 20.7 mg of [PhNMe$_2$H][B(C$_6$F$_5$)$_4$] (25.8 μmol) in 0.5 mL of C$_6$D$_5$Br. To this reaction mixture was added 50 μL of 1-methylcyclohexene (423 μmol, 17 equivalents) and 3 aliquots of 4 mL of H2. After 1.5 hours >90% was hydrogenated to methylcyclohexane ($^1$H-NMR)

Examples 15

8.0 mg of 1,1'-dimethylsilylbisindenyl zirconium dimethyl (Me$_2$SiInd$_2$ZrMe2), (19.6 μmol) and 15.6 mg of [PhNMe$_2$H][B(C$_6$F$_5$)$_4$] (19.6 μmol) were mixed in an NMR tube with 0.5 mL of C$_6$D$_5$Br. 16 μL of 1-methylcyclohexene and 5 mL of H$_2$ were added. Slow hydrogenation to methylcyclohexane was observed (≈60% conversion).

Example 16

9.5 mg of 1,1'-ethylenebisindenyl zirconium dibenzyl (EtInd$_2$ZrBz$_2$), (17.9 μmol) and 14.3 mg of [PhNMe$_2$H][B(C$_6$F$_5$)$_4$] (17.9 μmol) were reacted in 0.5 mL of C$_6$DF$_5$Br (NMR tube). 100 μL of 1-methylcyclohexene (846 μmol, 47 equivalents) was added. Portions of 5mL of H$_2$ were added by syringe. Hydrogenation to methylcyclohexane was observed. A conversion of 98% within an hour was achieved.

Example 17

A NMR tube was charged with 4.2 mg of [Cp(tBu)]$_2$ZrMe2 (11.5 μmol), 10 mg of [PhNMe$_2$H][B(C$_6$F$_5$)$_4$] (12.5 μmol) in 0.5 ml of bromobenzene-d$_5$. To this solution 120 mg of 2,4,4-trimethyl-2-pentene (1.07 mmol) was added. In 1 hour 30 ml of H$_2$ was added by syringe. The $^1$H-NMR spectrum of the solution showed full conversion of 2,4,4-trimethyl-2-pentene to 2,2,4-trimethylpentane.

Example 18

A NMR tube was charged with 4 mg of [Cp(nBu)]$_2$ZrMe$_2$ (11 μmol), 8.9 mg of [PhNMe$_2$H][B(C$_6$F$_5$)$_4$] (11.1 μmol) in 0.5 ml of bromobenzene-d5. To this solution 121 mg of 1-methylcyclohexene (1.26 mmol) was added. In 1 hour 35 ml of H$_2$ was added by syringe. The $^1$H-NMR spectrum of the solution showed full conversion of 1-methylcyclohexene to methylcyclohexane.

Example 19

A solution of 10 mg [Cp(nBu)]$_2$ZrMe$_2$ (27.5 μmol) in 0.5 g benzene-d6 was mixed with 22.5 mg [PhNMe$_2$H][B(C$_6$F$_5$)$_4$] (28 μmol) in 1.6 g toluene. A NMR tube was charged with a third of this mixture and 128 mg 1-methyl-cyclohexene (1.33 mmol). After addition of 10 ml H$_2$ by syringe 17.7% conversion of 1-methylcyclohexene to methylcyclohexane was observed in the $^1$H-NMR spectrum after 5 minutes. In 1 hour 52.4% conversion of 1-methylcyclohexene to methylcyclohexane was observed in the $^1$H-NMR spectrum (ca. 15 ml extra H$_2$ was added by syringe)

Comparative Example (C)

A solution of 10 mg [Cp(nBu)]$_2$ZrMe$_2$ (27.5 μmol) in 0.5 g benzene-d$_6$ was mixed with 1.6 g of a 10% methylalumoxane solution in toluene. A NMR tube was charged with a third of this mixture and 120 mg 1-methyl-cyclohexene (1.25 mmol) was added. After addition of 10 ml H$_2$ by syringe no conversion of 1-methylcyclohexene to methylcyclohexane was observed in the $^1$H-NMR spectrum after 2 hours.

What is claimed is:

1. A process for the selective hydrogenation of block copolymers having at least one poly(monovinylaromatic) block and at least one poly(conjugated diene) block which comprises contacting the block copolymers with hydrogen in the presence of a hydrogenation catalyst composition which comprises:

a) a metal compound cation of the formula $[(A)(E)MR_4]^+$ wherein M represents titanium, zirconium, or hafnium, A and E each represent ligands with structure I or II Structure I

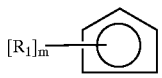

Structure II

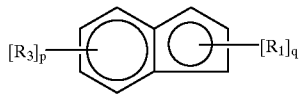

in which $R_1$ independently represents the same or different hydrocarbyl groups optionally containing heteroatoms, and $R_3$ independently represents the same or different hydrocarbyl groups optionally containing heteroatoms, or a halide, and in which $R_1$ and $R_3$ may be shared between A and E to provide a bridge, wherein m is an integer from 0–5, p is an integer from 0–4, and q is an integer from 0–3, herein $R_4$ represents hydrogen or a hydrocarbyl group optionally containing heteroatoms, with the proviso that if A and E are both ligands with the same structure, at least one of m, p or q is at least 1, and b) a non-coordinating stable anion.

2. The process according to claim 1 wherein the catalyst composition is present in a concentration, such that 0.1 to 0.75 g group 4 metal is present per 100 g copolymer.

3. The process of claim 1 wherein the metal compound cation has structure III

Structure III

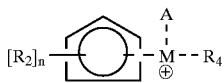

wherein M is titanium or zirconium; A is a ligand with structure I an III in which $R_1$ and $R_2$ are independently the same or different hydrocarbyl optionally containing a heteroatom and $R_3$ is hydrocarbyl, optionally containing a heteroatom, or a halide, $R_2$ may combine with $R_1$ or $R_3$ to form a bridge; and n is an integer from 1–5; and $R_4$ represents a hydrogen or hydrocarbyl group optionally containing heteroatoms.

4. The process of claim 3 wherein $R_2$ is a branched hydrocarbyl of from 3 to 15 carbon atoms and optionally containing heteroatoms.

5. The process of claim 4 wherein $R_2$ is tertiary-butyl or trimethylsilyl.

6. The process of claim 1 wherein the non-coordinating anion has the formula $[RB(Ar)_3^-]$ wherein Ar is a phenyl group substituted with halogen or alkoxy having 1 to 3 carbon atoms or a trihalogen substituted methyl group; and R is Ar, hydride, or hydrocarbyl group optionally containing heteroatoms.

7. The process of claim 6 wherein Ar is $C_6F_5$ or $3,5\text{-}(CF_3)_2C_6H_3$.

8. The process of claim 1 obtained by reacting a metal compound of formula $(A)(E)M(R_4)_2$, wherein A, E, M and $R_4$ are as defined in claim 1, with a salt of a non-coordinating stable anion.

9. The process of claim 8 wherein the salt of the non-coordinating stable anion is

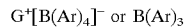

in which Ar is a phenyl group substituted with halogen or alkoxy having 1 to 3 carbon atoms or a trihalogen substituted methyl group and G is a cation capable of reacting with one $R_4$ of the metal compound to form a compound $GR_4$.

* * * * *